United States Patent [19]

Winstrom

[11] Patent Number: 4,745,923

[45] Date of Patent: May 24, 1988

[54] PROTECTION APPARATUS FOR PATIENT-IMPLANTABLE DEVICE

[75] Inventor: William L. Winstrom, Andover, N.J.

[73] Assignee: Intermedics, Inc., Angleton, Tex.

[21] Appl. No.: 799,804

[22] Filed: Nov. 20, 1985

[51] Int. Cl.⁴ .............................................. A61N 1/36
[52] U.S. Cl. .............................. 128/419 PG; 128/908
[58] Field of Search ........... 128/419 PG, 908, 419 PS

[56] References Cited

U.S. PATENT DOCUMENTS

| | | | |
|---|---|---|---|
| 3,518,986 | 7/1970 | Woods et al. .................. | 128/908 |
| 3,521,087 | 7/1970 | Lombardi ...................... | 128/908 |
| 3,603,811 | 9/1971 | Day ............................... | 128/908 |
| 3,968,802 | 7/1976 | Ballis ............................ | 128/908 |
| 4,082,097 | 4/1978 | Mann et al. ................... | 128/419 PS |
| 4,320,763 | 3/1982 | Money .......................... | 128/908 |
| 4,440,172 | 4/1984 | Langer .......................... | 128/419 D |

FOREIGN PATENT DOCUMENTS

| | | |
|---|---|---|
| 331893 | 8/1976 | Austria . |
| 3240280 | 5/1984 | Fed. Rep. of Germany . |
| 3308320 | 9/1984 | Fed. Rep. of Germany . |
| 612331 | 6/1978 | U.S.S.R. ............................. 128/908 |

Primary Examiner—William E. Kamm
Attorney, Agent, or Firm—Willian Brinks Olds Hofer Gilson & Lione Ltd.

[57] ABSTRACT

An electrical circuit is connected in series with a lead of an implantable heart pacemaker between the pacemaker and the heart to protect the pacemaker against high voltages and currents produced by defibrillators and other sources. The electrical circuit has a sensing resistor arranged between two normally conducting field effect transistors (FETs) all in electrical series with the pacemaker lead. When the voltage drop across the sensing resistor exceeds a predetermined positive or negative amplitude, a transistor becomes conductive and turns off the normal conduction channels of the FETs. An alternate, electrically conductive high-impedance path is switched in to limit the current flow to the pacemaker until the magnitude of the voltage across the sensing resistor drops to a safe level. The transistor then becomes non-conductive and the FETs become conductive re-establishing the normal low-impedance conduction path and effectively switching the alternate high-impedance path out of the circuit.

16 Claims, 2 Drawing Sheets

PROTECTION APPARATUS FOR PATIENT-IMPLANTABLE DEVICE

BACKGROUND OF THE INVENTION

The invention disclosed herein relates generally to protection devices used to protect other devices from damage or destruction resulting from voltage or current surges. In particular, the present invention relates to such a protection device which is implantable in the body of a patient with a heart pacemaker to protect the pacemaker against current surges, particularly those resulting from the operation of an external or implanted heart defibrillator.

It is well known that in many instances an implanted heart pacemaker can successfully regulate the otherwise faulty operation of a damaged or diseased heart. Generally, a typical pacemaker senses electrical activity or lack of such activity in the heart muscle, and supplies electrical stimulus pulses to the heart to stimulate contractions when necessary. The electrical stimulus pulses generated by a pacemaker, however, are ineffective to stop the lethal condition of fibrillation. However, it is well known that the application of a series of high-voltage pulses to the heart is often effective in arresting fibrillation. Of course it is desirable following defibrillation of the heart for the pacemaker to resume its normal regulatory role. A serious problem in this regard, however, is that without adequate protection against the large current flow induced by the application of high-voltage defibrillation pulses to the heart, a pacemaker can be damaged or destroyed. Obviously, from the standpoint of the patient's continued well being, this is a totally unacceptable consequence.

In the past, a number of attempts have been made to provide adequate protection against excessive currents and voltages for pacemakers and other medical devices such as electrocardiogram (ECG) amplifiers. For example, it is known to connect one or more zener diodes between the opposite leads of a pacemaker to limit the voltage differential therebetween.

However, as discussed in U.S. Pat. No. 4,320,763 to Money, this approach is not effective to limit the current flow between the heart tissue and the electrode at the distal end of the pacemaker lead. As a result, the heart tissue near the point of contact with the electrode can be severely damaged when high-voltage defibrillation pulses are applied to the heart. The U.S. Pat. No. 4,320,763 discloses that such tissue damage can be prevented by connecting a current limiting device such as a diode or a pair of field effect transistors (FETs) in series between a pacemaker output terminal and a distal electrode. However, it is apparent that the current limiting device thereby becomes a permanent part of the pacemaker circuit. When current limiting is not needed, for example during normal pacing operation, it is desirable to remove the current limiting device from the circuit to avoid unnecessary noise generation as well as loading effects.

An approach for protecting the pacemaker circuitry itself is disclosed in U.S. Pat. No. 4,440,172 to Langer. The U.S. Pat. No. 4,440,172 discloses an implantable pacemaker and defibrillator unit in which the pacemaker and defibrillator share common output and return lines. The pacemaker generates negative-going stimulus pulses and is protected against the positive-going high-voltage defibrillator pulses by a resistor and forward biased diode connected in series between the common output line and ground. This approach only provides limited protection to the pacemaker from unidirectional defibrillation pulses. Recent medical research has shown, however, that a number of benefits are obtained by using a bidirectional or "biphasic" pulse train to defibrillate the heart. Some of the benefits of "biphasic" defibrillation, which forms no part of the present invention, are discussed in Schuder, *Defibrillation of 100 kg Calves With Asymmetrical, Bidirectional, Rectangular Pulses,* Cardiovascular Research 419–426 (1984), and Jones, *Decreased Defibrillator-Induced Dysfunction With Biphasic Rectangular Waveforms,* Am. J. Physiol. 247 (Heart Circ. Physiol. 16): H792-H796 (1984).

U.S. Pat. No. 3,886,932 to Suessmilch discloses an approach in which a small sampling resistor is connected in series with a pacemaker lead. The resistor voltage is compared to a preselected reference voltage. If the resistor voltage exceeds the reference voltage, a switch in series with the resistor and lead is opened for a preselected period of time, after which it is closed and the voltage across the resistor again sampled. With this approach, there is no way to know what the current in the pacemaker lead will be when the switch closes at the end of the preselected time period. As a result, when the switch closes, it is possible that current flow in the lead will rise very rapidly. Even if the switch is quickly opened again, a current spike of unknown magnitude can be transmitted to the pacemaker, possibly causing damage, or causing the pacemaker sensor circuitry to misinterpret the status of the heart.

U.S. Pat. No. 4,102,348 to Hihara discloses an approach similar to that of Suessmilch except that the series switch is implemented as a bipolar transistor, the base voltage of which is supplied by the signal on the pacemaker lead through a resistive voltage divider. The state of the switch depends on the voltage of the signal on the lead. This approach, similarly to the Langer patent provides protection only against undirectional defibrillation pulses.

Accordingly, the present invention has as an object to provide a protection device that protects both a pacemaker or other implantable device and the heart tissue near a lead thereof against damage from high current and voltage levels, particularly those induced by the application of defibrillation pulses. In addition, the present invention has as an object to provide a protection device that switches into the circuit of a pacemaker or other implantable device to limit current in a lead of the device when current exceeds a safe limit, but which is effectively switched out of the circuit during normal operation of the device. Another object of the present invention is to provide a protection device that provides protection against high-voltage bidirectional or "biphasic" defibrillation pulses. Still another object of the present invention is to provide a protection device that prevents the transmission of possibly dangerous current and voltage spikes to the pacemaker or other device.

SUMMARY OF THE INVENTION

The above objects and advantages of the present invention are achieved by providing a protection device having a sensor, a switching unit, a controller, and an electrically conductive high-impedance path. The sensor senses the current flowing in at least one of the leads of the electrical device being protected, and generates a signal representative of the current. The controller responds to the signal and causes the switching unit to open the electrically conductive low-impedance path established by the lead when the current flowing in the lead exceeds a safe amplitude. When the electrically conductive low-impedance path is open, current is forced to flow in the electrically conductive high-impedance path where it is limited to a safe amplitude.

BRIEF DESCRIPTION OF THE DRAWINGS

An exemplary illustration of a presently preferred embodiment of the present invention is shown in the accompanying drawings, in which.

DETAILED DESCRIPTION OF A PRESENTLY PREFERRED EMBODIMENT

The novel features believed to be characteristic of the present invention are set forth in the appended claims. The invention itself, together with further objects and attendant advantages, will best be understood by reference to the following detailed description, which, when taken in conjunction with the accompanying drawings, discloses a presently preferred embodiment of the invention.

Figure 1:
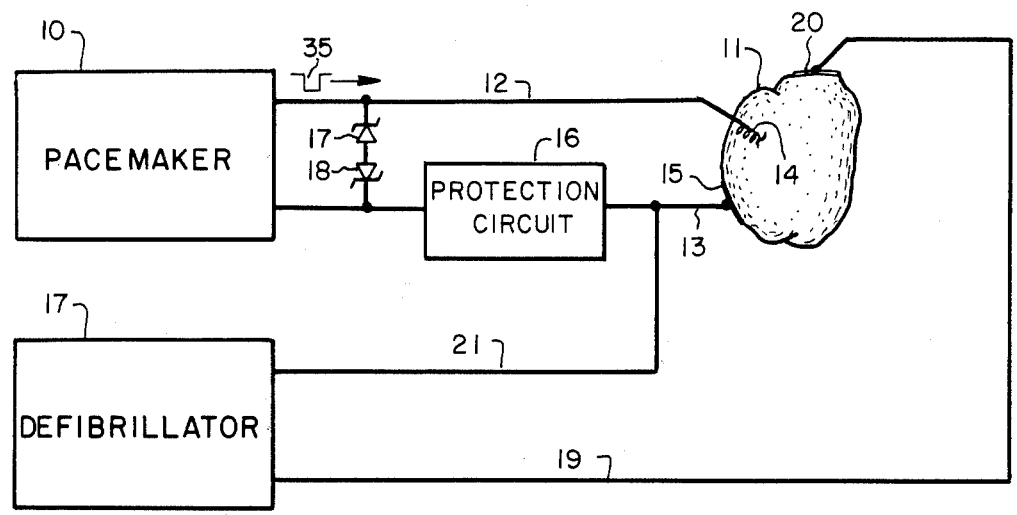
FIG. 1 is a block diagram illustrating a protection circuit comprising a presently preferred embodiment of the present invention in conjunction with a heart pacemaker and defibrillator unit.

Referring to FIG. 1, a heart pacemaker 10 implanted in the body of a patient is electrically connected in circuit with the patient's heart 11 via conventional electrically conductive pacing/sensing and return leads 12,13. Pacing/sensing lead 12 contains an electrically conductive barbed or screw-shaped pacing/sensing electrode 14 at its distal end for making firm electrical contact with the heart 11. Return lead 13 contains at its distal end a conductive patch 15 which may be sewn to the wall of the heart 11 to ensure a solid electrical connection. Electrically connected between the pacing/sensing and return leads 12,13 are oppositely polled first and second zener diodes 17,18 to limit the voltage differential between the terminals of the pacemaker 10. First zener diode 17 preferably limits the positive voltage differential to approximately +3 v. Second zener diode 18 preferably limits the negative differential to approximately −10 v. A protection circuit 16 comprising a presently preferred embodiment of the present invention is implanted with the pacemaker 10 and is electrically connected in series with return lead 13 and patch 15 between the heart 11 and the pacemaker 10.

In addition, a defibrillator 17, which may be either an external or an implanted unit, is also electrically connected in circuit with the heart 11. If implanted, the defibrillator 17 is electrically connected to the heart 11 via conventional electrically conductive output and return leads 19,21. Output lead 19 has attached to its distal end a conductive patch 20 which may be sewn to the wall of the heart 11. In this embodiment, return lead 21 is electrically connected at its distal end by any suitable means to return lead 13 between the heart 11 and the protection circuit 16 so that the pacemaker 10 and the defibrillator 17 share a common return lead to some extent. Of course, if the defibrillator 17 is an external unit, then no direct connections to the heart 11 are present. Instead, electrically conductive paddles of a type well known to those skilled in the art are supplied externally to the chest of a patient in the vicinity of the heart 11 as output and return electrodes.

It is understood that the pacemaker 10 and defibrillator 17 described above are exemplary devices only and that the protection circuit 16 comprising a presently preferred embodiment of the present invention will find use in many other applications where protection of a device against high voltages and currents is desirable.

Figure 2:
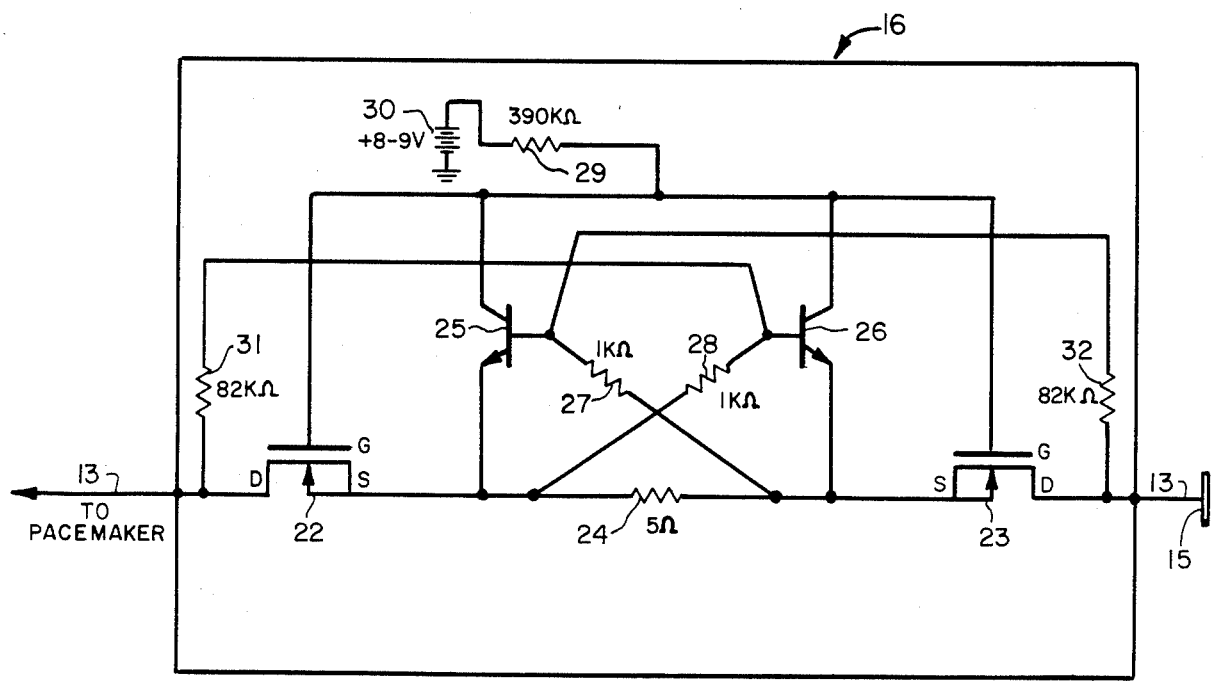
FIG. 2 is a schematic diagram of a protection circuit comprising a presently preferred embodiment of the present invention.

As illustrated in FIG. 2, the protection circuit 16 is electrically connected to conductive patch 15 via return lead 13. In series with return lead 13 are a first and a second field effect transistor (FET) 22, 23 and a 5 ohm sensing resistor 24. The drain of the second FET 23 connects to return lead 13 on the heart 11 side. The source of the second FET 23 connects to one end of the sensing resistor 24 and the source of the first FET 22 connects to the opposite end. The drain of the first FET 16 connects to the opposite end of return lead 13 on the pacemaker 10 side. The gates of the first and second FETs 22,23 are connected in parallel to one end of a 390K ohm current limiting resistor 29 and to the collectors of first and second parallel bipolar transistors 25,26. The other end of the 390K ohm current limiting resistor 29 connects to a DC voltage source 30.

The emitter of the first bipolar transistor 25 connects to the source of the first FET 22. The emitter of the second bipolar transistor 26 connects to the source of the second FET 23. A first 1K ohm resistor 27 connects the base of the first bipolar transistor 25 with the emitter of the second bipolar transistor 26. Likewise, a second 1k ohm resistor 28 connects the base of the second bipolar transistor with the emitter of the first bipolar transistor 25. The base of the first bipolar transistor 25 also connects to the drain of the second FET 23 through a first 82K ohm resistor 32. Likewise, the base of the second bipolar transistor 26 connects to the drain of the first FET 22 through a second 82K ohm resistor 31.

The DC voltage source 30 is preferably derived by a conventional voltage multiplication technique, for example employing switched capacitors, and a miniature long-life battery such as a lithium cell to obtain an output of 8–9VDC. The first and second FETs 22,23 are preferably n-channel FETs and are preferably able to withstand voltages in the 1000 volt range, as well as substantial continuous and peak currents. Also, the first and second FETs 22,23 preferably exhibit very fast turn-off times and good conduction at a relatively low threshold voltage. Further, the FET's are preferably of the type in which the source is internally connected to the substrate. Commercially available Motorola MTM-1N100 n-channel FETs and equivalents, for example, have been found to possess the desired characteristics, and are suitable for use. First and second bipolar transistors 21,22 are preferably conventional, commercially available NPN transistors such as, for example, 2N2222A transistors. The 5 ohm sensing resistor may be any suitable precision resistor.

It should be apparent to those skilled in the art that although the foregoing describes a presently preferred embodiment of the present invention in terms of a positive DC voltage source, n-channel FETS, and NPN bipolar transistors, a protection circuit employing a negative DC voltage source, p-channel FETs, and PNP bipolar transistors constitutes an equally preferred embodiment.

Operation of the protection circuit 16 of FIG. 2 will now be described. In the normal pacing/sensing mode, the pacing/sensing lead 12 and pacing/sensing electrode 14 conduct electrical signals generated by the heart 11 to the pacemaker 10. If the pacemaker 10 fails to detect electrical activity in the heart, it generates one or more electrical stimulus pulses 35. A typical stimulus pulse 35 might be, for example, a short duration, rectangular −8 V pulse. The pacing/sensing lead 12 and the pacing/sensing electrode 14 conduct these stimulus pulses 35 to the heart 11 to hopefully stimulate cardiac activity. In the normal pacing/sensing mode, current in the pacing/sensing and return leads 12,13 typically ranges from approximately 0.1 to 35 milliamperes. The gates of the first and second FETs 22,23 are held at a positive voltage in excess of the conduction threshold by the DC voltage source 30. The potential at the sources of the first and second FETs 22,23 is substantially lower than at the gates and the first and second FETs conduct current like closed switches with very little impedance. Assuming the current in the return lead 13 is, as stated above, no more than about ±35 milliamperes, the voltage drop across the 5 ohm sensing resistor 24 is insufficient to forward bias the base-emitter junction of either the first or the second bipolar transistor 25,26 so that neither transistor is conductive. Thus, in the normal pacing/sensing mode, current continues to flow through the low impedance path established by the return lead 13, the 5 ohm sensing resistor 24, and the first and second FETs 22,23. The high-impedance portion of the protection circuit 16 comprising the 82K ohm and 1K ohm resistors 27, 28, 31, 32 is effectively switched out of the circuit.

Figure 3:
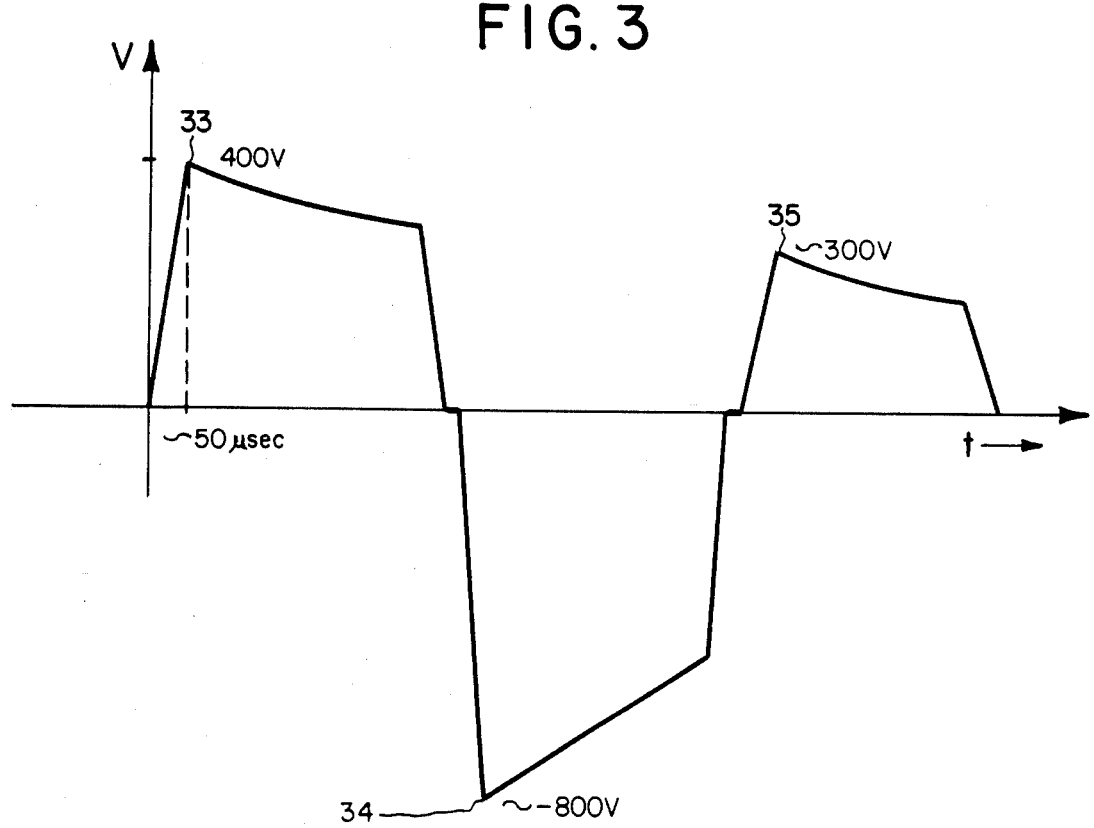
FIG. 3 is a graph of voltage vs. time illustrating a typical biphasic defibrillation pulse train.

However, when the heart 11 begins to fibrillate, the condition is sensed by the delibrillator 17 or other monitoring equipment. In response, the defibrillator 17 generates a series of high-voltage pulses which are conducted to the heart 11 via lead 20 or an external paddle. FIG. 3 illustrates a typical biphasic defibrillation pulse train which has been found to be particularly effective in arresting fibrillation, and which in addition has been found to impart beneficial post-defibrillation healing effects to the heart. The biphasic pulse train itself forms no part of the present invention but is included herein for the purpose of illustrating various features of the present invention.

The typical biphasic defibrillation pulse train may consist of an initial positive pulse 33 rising to a peak of approximately 400 volts in approximately 50 microseconds, having an on-time of 2–5 milliseconds, and a turn off time of approximately 10 microseconds. A second negative pulse 34 of greater magnitude typically follows the initial positive pulse 33. The second negative pulse 34 may rise to a peak of approximately −800 volts in approximately 50 microseconds, have an on-time of 5–8 milliseconds, and a turn-off time of approximately 10 microseconds. In some instances, a final positive pulse 35 has been found to impart beneficial healing effects to the defibrillated heart. The final positive high-voltage pulse 35 may rise to a peak voltage of approximately 300 volts in approximately 50 microseconds, have an on-time of 2–5 milliseconds, and a turn-off time of approximately 10 microseconds.

Figure 4:
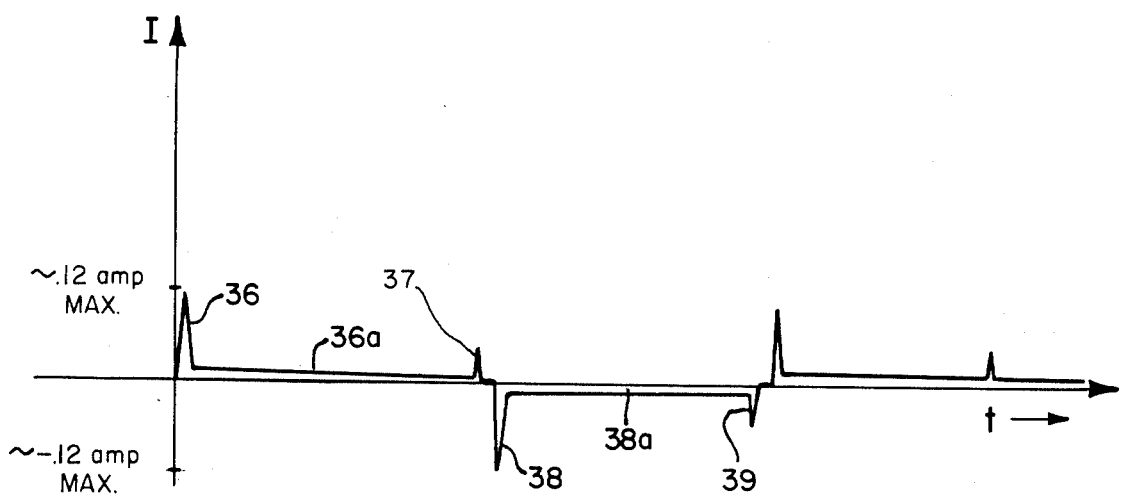
FIG. 4 is a graph of current vs. time synchronized with the graph of FIG. 3 and illustrating the current typically produced in a pacemaker lead by the pulse train of FIG. 4 with the protection circuit comprising a presently preferred embodiment of the present invention arranged as shown in FIGS. 1 and 2.

When the initial positive pulse 33 is applied to the heart 11, the positive potential at the conductive patch 15 raises rapidly. As illustrated in FIG. 4, this in turn causes the positive current in return lead 13 to rise rapidly, in turn causing the positive voltage drop across the 5 ohm sensing resistor 24 to rise rapidly. When the amplitude of the positive current flow through the sensing resistor 24 reaches approximately 0.12 amperes resulting in a voltage drop across the sensing resistor 24 of approximately 0.6 volts, the base-emitter junction of the first bipolar transistor 25 becomes forward biased. The first bipolar transistor 25 then becomes conductive and electrically connects the sources and gates of the first and second FETs 22,23. This in turn causes the conduction channels between the sources and drains of the first and second FETs 22,23 to collapse. However, because each of the FETs has its source and substrate permanently connected internally, at high currents each acts as a diode forward biased between the source and drain. Thus, the second FET 23 acts as a reverse biased diode or open switch to the positive current in return lead 13 while the first FET 22 acts as a forward biased diode to the positive current. As a result, when the normal conduction paths of the first and second FETs 22,23 collapse, the high-impedance portion of the protection circuit 16 is switched in and an alternate high-impedance conduction path in series with the return lead 13 is established. This path comprises the 82K ohm resistor 32, the 1K ohm resistor 27, the 5 ohm sensing resistor 24, and the first FET 22. The switching of the high-impedance conduction path results in a sharp drop 36 in current to a safe maximum current 36a of approximately 4–5 milliamperes.

The first bipolar transistor 25 remains conductive until the positive voltage at the conductive patch 15 drops below approximately 50 volts. At this point, the current flowing in the high-impedance conduction path is insufficient to forward bias the baseemitter junction of the first bipolar transistor 25, which ceases to conduct. This in turn disconnects the sources and gates of the first and second FETs 22,23, which re-establishes the source to drain conduction channels and allows the FETs 22,23 to once again conduct as closed switches. Because the positive potential at the conductive patch 15 is still approximately 50 volts at this time, a small current surge 37 having a peak magnitude substantially less than the maximum safe amplitude of approximately 0.12 amperes occurs.

When the second negative biphasic pulse 34 is applied to the heart 11, the magnitude of the negative potential at the conductive patch 15 increases rapidly. In turn, the magnitude of the negative current flowing through and the voltage across the 5 ohm sensing resistor 24 also increase rapidly. When the magnitude of the negative current reaches approximately −0.12 amperes with a corresponding voltage drop of −0.6 volts across the 5 ohm sensing resistor 24, the base-emitter junction of the second bipolar transistor 26 becomes forward biased. The second bipolar transistor 26 then becomes conductive and electrically connects the sources and gates of the first and second FETs 22,23. This in turn causes the source to drain conduction paths in the FETs 22,23 to collapse. In this case, the first FET 22 acts as a reverse biased diode or open switch to the negative current while the second FET 23 acts as a forward biased diode. As a result, the high-impedance portion of the protection circuit 16 is switched in and an alternate high-impedance conduction path for the negative current is established. This path comprises the 82K ohm resistor 31, the 1K ohm resistor 28, the 5 ohm sensing resistor 24, and the second FET 23. The 82K ohm resistor 31, the 1K ohm resistor 28, the 5 ohm sensing resistor 24, the collector-emitter path of the second bipolar transistor 26, and the 390K ohm resistor 29 establish a parallel high-impedance path for the negative current. The switching in of the parallel high-impedance conduction paths results in a sharp decline 38 in the current of the negative current to a safe maximum amplitude 38a of less than 10 milliamperes as illustrated in FIG. 4.

The second bipolar transistor 26 remains conductive until the magnitude of the negative potential at the conductive patch 15 drops to approximately −50 volts. At this point, the negative current flowing in the parallel, high-impedance paths is insufficient to forward bias the base-emitter junction of the second bipolar transistor 26, which ceases to conduct. This in turn disconnects the sources and gates of the first and second FETs 25,26, which re-establishes the source to drain conduction channels and causes the FETs 25,26 to again conduct as closed switches. Because the negative potential at the conductive patch 15 is still approximately −50 volts at this time, a small negative current surge 39 having a peak magnitude substantially less than the maximum safe amplitude of approximately −0.12 amperes occurs.

Operation of the protection circuit 16 for subsequent positive and negative defibrillation pulses including pulse 35 of FIG. 3 is identical. In addition, the presently preferred embodiment of the protection circuit 16 operates the same regardless of whether the defibrillator pulses are directly applied to the heart 11 as illustrated in FIG. 1, or are applied externally via conductive paddles as described above. Operation of the presently preferred embodiment of the protection circuit is also independent of the manner of pacing and sensing employed.

Of course it should be understood that the apparatus described herein in detail is merely illustrative of various aspects of the present invention and is not intended to be limiting. Various changes to the preferred embodiments described herein will be apparent to those skilled in the art. Such changes and modifications can be made without departing from the spirit and scope of the present invention. It is, therefore, intended that such changes and modifications be covered by the following claims and their equivalents.

I claim:
1. An apparatus for protecting an implantable electrical device having a plurality of electrically conductive terminals, including output and return terminals and electrically conductive leads connected to said terminals against excessive currents comprising:
    means connected to form an electrically conductive low-impedance path for connection in circuit with at least one of said leads;
    means connected to form an electrically conductive high-impedance path for connection in circuit with said at least one lead;
    means for generating a signal representative of the current flowing in said low-impedance path;
    switch means for opening and closing said low-impedance path; and
    means responsive to said signal representative of said current for controlling said switch means to open said low-impedance path when said current exceeds a predetermined level so that said current flows in said high-impedance path, whereby the current flowing into said electrical device is limited to a safe level.
2. The apparatus of claim 1 further comprising means for limiting the maximum voltage between said output and return terminals of said electrical device to a predetermined safe level.
3. The apparatus of claim 1 wherein said means for generating a signal representative of said current comprises a sensing resistor.
4. The apparatus of claim 1 wherein said switch means and said means for generating a signal representative of current are connected in electrical series in said low-impedance path.
5. The apparatus of claim 1 wherein said means for controlling said switch means comprises first control means for controlling said switch means to open said low-impedance path when said current exceeds a predetermined positive amplitude, and second control means for controlling said switch means to open said low-impedance path when said current exceeds a predetermined negative amplitude.
6. The apparatus of claim 5 wherein:
    said switch means comprises first and second series-connected field effect transistors;
    said first control means comprises a first transistor connected between the gates and sources of said first and second field effect transistors to electrically connect said gates and sources when said current exceeds a predetermined positive amplitude; and
    said second control means comprises a second transistor connected between the gates and sources of said first and second field effect transistors to electrically connect said gates and sources when said current exceeds a predetermined negative amplitude.
7. A patient implantable apparatus for assisting the proper functioning of a patient's heart, comprising:
    pacemaker means including:
    a plurality of electrically conductive terminals;
    means connected to at least one of said terminals for sensing signals representative of the activity of the patient's heart; and
    means connected to at least one of said terminals for generating electrical stimulus signals to stimulate heart activity;
    a plurality of electrically conductive leads for connection to the patient's heart, and to said terminals for communicating said electrical signals representative of the activity of the heart to the pacemaker means, and for communicating said electrical stimulus signals from said pacemaker means to the heart; and
    pacemaker protection means, comprising:
    means connected to form an electrically conductive low-impedance path for connection in circuit with at least one of said leads;
    means connected to form an electrically conductive high-impedance path for connection in circuit with said at least one lead;
    means for generating a signal representative of the current flowing in said low-impedance path;
    switch means for opening and closing said low-impedance path;

means responsive to said signal representative of said current for controlling said switch means to open said low-impedance path when said current exceeds a predetermined level so that said current flows in said high-impedance path, whereby the current flowing into said pacemaker means is limited to a safe level.

8. The apparatus of claim 7 further comprising means for limiting the maximum voltage between said terminals of said pacemaker means to a predetermined safe level.

9. The apparatus of claim 7 wherein said means for generating a signal representative of said current comprises a sensing resistor.

10. The apparatus of claim 7 wherein said switch means and said means for generating a signal representative of current are connected in electrical series in said low-impedance path.

11. The apparatus of claim 10 wherein:
said switch means comprises first and second series-connected field effect transistors;
said first control means comprises a first transistor connected between the gates and sources of said first and second field effect transistors to electrically connect said gates and sources when said current exceeds a predetermined positive amplitude; and
said second control means comprises a second transistor connected between the gates and sources of said first and second field effect transistors to electrically connect said gates and sources when said current exceeds a predetermined negative amplitude.

12. The apparatus of claim 7 wherein said means for controlling said switch means comprises first control means for controlling said switch means to open said low-impedance path when said current exceeds a predetermined positive amplitude, and second control means for controlling said switch means to open said low-impedance path when said current exceeds a predetermined negative amplitude.

13. A protection apparatus for a patient-implantable electrical device having means operative to sense electrical sense signals indicative of activity of a selected body part, means operative to generate electrical stimulus signals to stimulate said body part, and at least one electrically conductive lead for connecting said device to said body part, comprising:
electrically conductive low-impedance path means for connection in circuit with said lead for conducting said sense and stimulus signals between said device and said body part;
electrically conductive high-impedance path means for connection in circuit with said lead for limiting the current flowing between said body part and said device to protect said device against damage; and
means responsive to the current flowing in said low-impedance path to cause said current to flow in said low-impedance path when it is below a predetermined value in excess of the minimum stimulation level of said body part and to flow in said high-impedance path when it is in excess of that value so that the current flowing between said organ and said device is limited to a safe level.

14. The protection apparatus of claim 13 wherein said means responsive to current flowing in the low-impedance path comprises:
means for generating a signal representative of the current flowing in said low-impedance path;
switch means for opening and closing said low-impedance path; and
means responsive to said signal representative of said current for controlling said switch means to open said low-impedance path when said current exceeds said predetermined value so that said current flows in said high-impedance path, whereby the current flowing into said electrical device is limited to a safe level.

15. The protection apparatus of claim 14 wherein said means for controlling comprises first control means for controlling said switch means to open said low-impedance path when said current exceeds said predetermined value with positive polarity and second control means for controlling said switch means to open said low-impedance path when said current exceeds said predetermined value with negative polarity.

16. The protection apparatus of claim 13 wherein said low-impedance and high-impedance path means are adapted for parallel connection in circuit with said lead.

* * * * *